US012590284B2

(12) United States Patent
Méndez Herrera et al.

(10) Patent No.: US 12,590,284 B2
(45) Date of Patent: Mar. 31, 2026

(54) SYSTEM FOR THE CAPTURE AND PURIFICATION OF CO₂ AND PURIFICATION UNIT OF SAID SYSTEM

(71) Applicant: INSTITUTO DE TRANSFERENCIA TECNOLÓGICA Y EMPRENDIMIENTO LTDA, Concepción (CL)

(72) Inventors: Paola Andrea Méndez Herrera, Concepción (CL); Margarita del Rosario Sepúlveda Reyes, Hualpén (CL); Artemio Héctor Huenuqueo Herrera, Concepción (CL); Erwin Hugo Sepúlveda Sandoval, Concepción (CL); Violeta Alejandra Torres Sepúlveda, Hualpén (CL)

(73) Assignee: INSTITUTO DE TRANSFRENCIA TECNOLÓGICA Y EMPRENDIMIENTO LTDA., Concepción (CL)

( * ) Notice: Subject to any disclaimer, the term of this patent is extended or adjusted under 35 U.S.C. 154(b) by 396 days.

(21) Appl. No.: 18/016,317

(22) PCT Filed: May 18, 2021

(86) PCT No.: PCT/CL2021/050042
§ 371 (c)(1),
(2) Date: Mar. 9, 2023

(87) PCT Pub. No.: WO2022/011485
PCT Pub. Date: Jan. 20, 2022

(65) Prior Publication Data
US 2023/0313118 A1      Oct. 5, 2023

(30) Foreign Application Priority Data
Jul. 14, 2020      (CL) .................................. 1865-2020

(51) Int. Cl.
*B01D 53/02*          (2006.01)
*B01D 53/04*          (2006.01)
(Continued)

(52) U.S. Cl.
CPC ......... *C12M 47/12* (2013.01); *B01D 53/0438* (2013.01); *B01D 53/0446* (2013.01);
(Continued)

(58) Field of Classification Search
CPC ........ B01D 2253/102; B01D 2253/106; B01D 2253/108; B01D 2253/204;
(Continued)

(56) References Cited

U.S. PATENT DOCUMENTS 8,591,627 B2 * 11/2013 Jain ...................... B01D 53/047
95/52
8,696,804 B2 * 4/2014 Ihms ................. B01D 53/1475
95/183
(Continued)

*Primary Examiner* — Christopher P Jones
(74) *Attorney, Agent, or Firm* — Procopio, Cory, Hargreaves & Savitch LLP

(57) ABSTRACT

The present invention provides a system for the capture and purification CO₂ and a purification unit for said system, wherein said purification unit comprises: a first filter having a first container and a first filler material; a second filter having a second container and a second filler material, downstream of said first filter; a third filter having a third container and a third filler material, downstream of said second filter, said third filter having, additionally, a heating element thermally coupled to said third filler material; and control means of said heating element; wherein said first filler material is silica; wherein said second filler material is zeolite; and wherein said third filler material is a metal-organic framework modified with activated carbon.

12 Claims, 3 Drawing Sheets

(51) Int. Cl.
    *B01J 20/10*      (2006.01)
    *B01J 20/18*      (2006.01)
    *B01J 20/20*      (2006.01)
    *B01J 20/22*      (2006.01)
    *C12M 1/00*      (2006.01)

(52) U.S. Cl.
    CPC ........ *B01D 53/0454* (2013.01); *B01J 20/103*
        (2013.01); *B01J 20/18* (2013.01); *B01J 20/20*
        (2013.01); *B01J 20/226* (2013.01); *B01D*
        *2253/102* (2013.01); *B01D 2253/108*
        (2013.01); *B01D 2253/204* (2013.01); *B01D*
        *2257/504* (2013.01); *B01D 2259/40088*
        (2013.01); *B01D 2259/403* (2013.01); *B01D*
        *2259/414* (2013.01)

(58) Field of Classification Search
    CPC ......... B01D 2256/22; B01D 2257/504; B01D
        2259/40009; B01D 2259/40088; B01D
        2259/403; B01D 2259/414; B01D 53/0423; B01D 53/0438; B01D 53/0446;
B01D 53/0454; B01D 53/0462; B01D
53/44; B01J 20/103; B01J 20/165; B01J
20/18; B01J 20/20; B01J 20/226; B01J
20/3204; B01J 20/3236; B01J 2220/603;
C01B 32/50; C12F 3/02; C12M 47/12;
Y02C 20/40; Y02P 20/151
See application file for complete search history.

(56)         References Cited

U.S. PATENT DOCUMENTS

| | | | |
|---|---|---|---|
| 10,434,457 B2 * | 10/2019 | Mansour ................ | B01J 20/226 |
| 2015/0053080 A1 * | 2/2015 | Boehringer ............. | B01J 39/00 |
| | | | 422/616 |
| 2017/0136400 A1 * | 5/2017 | Sundaram .......... | B01D 53/0423 |
| 2018/0236395 A1 * | 8/2018 | Naito .................... | B01J 20/165 |
| 2019/0168417 A1 * | 6/2019 | Fadhel ................. | B01D 53/62 |
| 2022/0112598 A1 * | 4/2022 | Iyer .................... | C23C 16/4412 |

* cited by examiner

SYSTEM FOR THE CAPTURE AND PURIFICATION OF CO$_2$ AND PURIFICATION UNIT OF SAID SYSTEM

TECHNICAL FIELD OF INVENTION

The present invention relates to the field of physical and chemical processes and apparatus in general, specifically to apparatus and systems for capturing and purifying gases, and in particular provides a system for the capture and purification of CO$_2$ and a purification unit for said system.

BACKGROUND OF THE INVENTION

In different industries, particularly in alcoholic fermentation industries, it is desirable to have a way to reuse greenhouse gases and eliminate their emission into the atmosphere.

Carbon dioxide capture technologies based on absorption and adsorption processes in fixed installations are known in the state of the art. However, these solutions have the disadvantage of involving a high energy cost due to the pressure and/or temperature conditions in which they are developed. In addition, most of these solutions are focused on the capture of post-combustion gases, but there is no known history of their efficiency in the capture of gases from fermentation processes.

In the state of the art, some solutions are known that allow the capture of gases from fermentation processes. For example, document CL 2013-03353, from the same applicant of the present application, describes a system and a method for capturing CO$_2$ from fermentation processes such as the production of wines, beers, and dairy products. Said system comprises a gas inlet line, an accumulation unit, and a storage unit. However, this document does not describe the presence of a purification unit for the captured gas.

On the other hand, document CN102851163 describes a system for the capture and purification of CO$_2$ from fermentation processes. The system described in this paper has a two-stage chemical purification unit. In the purification unit, the gas first passes through a demister to remove foams. The gas then flows through a two-stage scrubber, a first stage in which the gas is washed with a potassium permanganate solution to remove aldehydes, and a second stage in which the gas is washed with sodium bicarbonate to remove acidic substances. As described therein, the purification unit is based on chemical processes that make intensive use of water.

Consequently, a system for the capture and purification of CO$_2$ is required, as well as a purification unit for said system, that allows the purification based on essentially physical processes with low water consumption.

SUMMARY OF THE INVENTION

The present invention provides a system for the capture and purification of CO$_2$ comprising a gas inlet line; an accumulation unit, having an inlet connected to said gas inlet line and an outlet; a purification unit, having an inlet connected downstream of said accumulation unit and an outlet; and a storage tank, having an inlet connected downstream of said purification unit which is characterized in that said purification unit comprises: a first filter having a first container and a first filler material; a second filter having a second container and a second filler material, downstream of said first filter; a third filter having a third container and a third filler material, downstream of said second filter, said third filter additionally having a heating element thermally coupled to said third filler material; and means for controlling said heating element; wherein said first filler material is silica; wherein said second filler material is zeolite; and wherein said third filler material is a metal-organic framework modified with activated carbon.

In a preferred embodiment, the system is characterized in that it comprises a plurality of gas inlet lines arranged in a parallel manner, and in that said accumulation unit is connected to each of said gas inlet lines of said plurality. In a more preferred embodiment, the system is characterized in that it further comprises a plurality of unidirectional valves, each of said unidirectional valves operatively connected to a corresponding gas inlet line of said plurality of gas inlet lines. In another more preferred embodiment, the system is characterized in that it further comprises a coupling, having a plurality of inlets and an outlet; wherein each said inlets of said coupling is connected to a corresponding gas inlet line and in that said outlet of said coupling is connected to said inlet of said accumulation unit. In a still more preferred embodiment, the system is characterized in that it further comprises a compressor operatively connected between said outlet of said coupling and said inlet of said accumulation unit.

In another preferred embodiment, the system is characterized in that said metal-organic framework has a metal center and an organic ligand, wherein said metal center is selected from the group consisting of Ni, Zn, Cu, as well as combinations thereof; and wherein said organic ligand is selected from the group consisting of 1,4-benzenedicarboxylate (H$_2$BDC), tetrabromo-catechol (H$_2$TBC), as well as a combination thereof. In an even more preferred embodiment, said metal-organic framework is Ni-MOF-5.

In a further preferred embodiment, the system is characterized in that said heating element is selected from the group consisting of heating tapes, heating plates, incandescent filaments, infrared lamps, electrical resistors, as well as a combination thereof.

In another preferred embodiment, the system is characterized in that said control means are selected from the group consisting of thermostats, optocouplers, PID temperature controllers, ON-OFF temperature controllers, as well as combinations thereof.

In a preferred embodiment, the system is characterized in that it further comprises:
- a first pressure sensor operatively connected to said gas inlet line and a first valve operatively connected to said gas inlet line downstream of said first pressure sensor;
- a second pressure sensor operatively connected to said outlet of said accumulation unit and a second valve operatively connected to said outlet of said accumulation unit downstream of said second pressure sensor;
- a first CO$_2$ partial pressure sensor operatively connected to said inlet of said purification unit and a third valve operatively connected to said inlet of said purification unit downstream of said first CO$_2$ partial pressure sensor; and
- a second CO$_2$ partial pressure sensor operatively connected to the outlet of said purification unit and a fourth valve operatively connected to said outlet of said purification unit downstream of said second CO$_2$ partial pressure sensor.

In a more preferred embodiment, the system is characterized in that it further comprises a vent valve operatively connected to said outlet of said purification unit downstream of said second CO$_2$ partial pressure sensor.

In another preferred embodiment, the system is characterized in that it comprises a compressor between said purification unit and said storage unit.

In a further preferred embodiment, the system is characterized in that said gas inlet line further comprises coupling means to a fermentation vessel, said coupling means comprising a cylindrical bellows.

The present invention provides, in another subject matter of invention, a purification unit for a system for the capture and purification of gases characterized in that it comprises: a first filter having a first container and a first filler material; a second filter having a second container and a second filler material, downstream of said first filter; a third filter having a third container and a third filler material, downstream of said second filter, said third filter having, additionally, a heating element thermally coupled to said third filler material; and control means of said heating element; wherein said first filler material is silica; wherein said second filler material is zeolite; and wherein said third filler material is a metal-organic framework modified with activated carbon.

In a preferred embodiment, the purification unit is characterized in that said metal-organic framework has a metal center and an organic ligand, wherein said metal center is selected from the group consisting of Ni, Zn, Cu, as well as combinations thereof; and wherein said organic ligand is selected from the group consisting of 1,4-benzenedicarboxylate acid ($H_2$BDC), tetrabromo-catechol ($H_2$TBC), as well as a combination thereof. In an even more preferred embodiment, said metal-organic framework is Ni-MOF-5.

In another preferred embodiment, the purification unit is characterized in that said heating element is selected from the group consisting of heating tapes, heating plates, incandescent filaments, infrared lamps, electrical resistors, as well as a combination thereof.

In a further preferred embodiment, the purification unit is characterized in that said control means are selected from the group consisting of thermostats, optocouplers, PID temperature controllers, ON-OFF temperature controllers, as well as combinations thereof.

DETAILED DESCRIPTION OF THE INVENTION

The system (1) and the purification unit (4) which are the subject matter of the present invention will be described in detail below, referring for this purpose to the Figures accompanying the present application.

Figure 1:
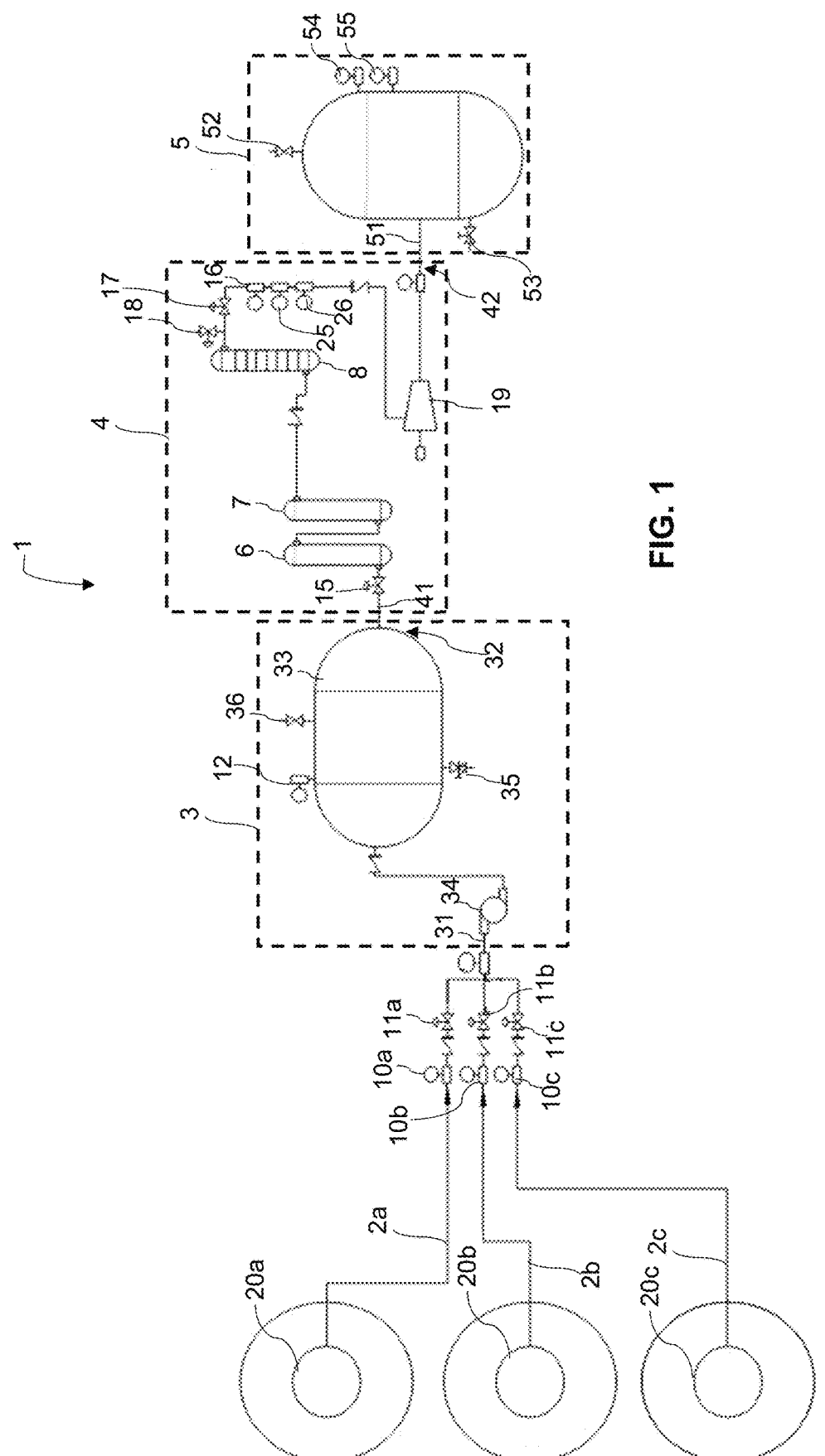
FIG. 1 shows a schematic illustration of a first embodiment of the system which is the subject matter of the present invention.

As illustrated schematically in FIG. 1, and without limiting the scope of the present invention, the present invention provides, in a first subject matter of the invention, a system (1) for the capture and purification of $CO_2$ comprising a gas inlet line (2); an accumulation unit (3), having an inlet (31) connected to said gas inlet line (2) and an outlet (32); a purification unit (4), having an inlet (41) connected downstream of said accumulation unit (3) and an outlet (42); and a storage tank (5), having an inlet (51) connected downstream of said purification unit (4). Said system (1) is characterized in that said purification unit (4) comprises: a first filter (6) having a first container and a first filler material; a second filter (7) having a second container and a second filler material, downstream of said first filter (6); a third filter (8) having a third container (81) and a third filler material, downstream of said second filter (7), said third filter (8) additionally having a heating element (82) thermally coupled to said third filler material; and control means (9) of said heating element (82); wherein said first filler material is silica; wherein said second filler material is zeolite; and wherein said third filler material is a metal-organic framework modified with activated carbon.

In the context of the present invention, without limiting the scope of the present invention, it will be understood that relative directions, such as anterior, posterior, upstream, downstream, among others, will be understood as referring to the direction of circulation of the gas inside the system (1) when the same is normally in use. In this sense, without limiting the scope of the present invention, it should be understood that, in use, the gas will circulate from the gas inlet line (2) towards the storage tank (5), passing through the accumulation unit (3) and the purification unit (4). Additionally, it should be understood that one element may be downstream of another, even if there are additional elements between them. In this sense, for example and without limiting the scope of the present invention, it should be understood that the purification unit (4) is downstream of the gas inlet line (2), even though between them may be disposed, at least and without limiting the scope of the present invention, the accumulation unit (3).

Although the present invention was developed for the capture and purification of $CO_2$ from fermentation processes, the origin of said gas does not limit the scope of the present invention. For example, and without limiting the scope of the present invention, said gas may come from fermentation processes, degradation processes, or a combination of the foregoing.

In a preferred embodiment, said $CO_2$ comes from fermentation processes. In the context of the present invention, a fermentation process, or fermentative process, will be understood as any industrial process involving the use of one or more microorganisms and that produces $CO_2$ as a waste product. Said fermentative process, without limiting the scope of the present invention, may be aerobic or anaerobic, as well as a combination thereof. Additionally, the nature of said one or more microorganisms involved does not limit the scope of the present invention. Examples of fermentative processes, without limiting the scope of the present invention, are wine production, beer production, and dairy production.

The system (1), which is the subject matter of the present invention, comprises a gas inlet line (2). Said gas inlet line (2) is operatively connected to the gas source (which is not part of the system which is the subject matter of the present invention) from which $CO_2$ is to be captured and purified.

However, in certain preferred embodiments, said system (1) may comprise a plurality of gas inlet lines (2a, 2b, 2c). In the latter preferred embodiment, without limiting the scope of the present invention, the accumulation unit (3) forming part of the system (1) is operatively connected to each of said gas inlet lines (2a, 2b, 2c) forming part of said plurality.

In the context of the present invention, the term plurality is to be understood as meaning two or more of the elements to which reference is made. In this sense, the number of elements forming part of said plurality does not limit the scope of the present invention. Furthermore, it should be understood that said elements forming part of said plurality may be identical or different from each other without limiting the scope of the present invention.

The operative connection between said accumulation unit (3) and each of said gas inlet lines (2a, 2b, 2c) forming part of said plurality may be obtained by any manner known to a person with average knowledge in the technical field. For example, and without limiting the scope of the present invention, each of said gas inlet lines (2a, 2b, 2c) may be directly connected to a corresponding inlet of said accumulation unit (3). However, in other preferred embodiments and without limiting the scope of the present invention, it is possible to provide a coupling having a plurality of inlets and an outlet. In this preferred embodiment, without limiting the scope of the present invention, each of said inlets of said coupling is connected to a corresponding gas inlet line (2a, 2b, 2c) and, additionally, said outlet of said coupling is connected to said inlet (31) of said accumulation unit (3). This preferred embodiment, without limiting the scope of the present invention, is advantageous in that it allows giving a hub-type modular structure to the system (1) which is the subject matter of the present invention.

Options for a gas inlet line (2) will be described below. It is to be understood, in those preferred embodiments which include a plurality of inlet lines (2a, 2b, 2c), that each of said optional embodiments may be applied to each of the gas inlet lines (2a, 2b, 2c) forming part of the plurality without limiting the scope of the present invention.

The shape, length, and dimensions of said gas inlet line (2) do not limit the scope of the present invention. In a preferred embodiment, without limiting the scope of the present invention, said gas inlet line (2) may comprise one or more ducts connected to each other. Said ducts may be rigid or flexible, as well as a combination thereof, without limiting the scope of the present invention. Additionally, the material from which said gas inlet line (2) is manufactured does not limit the scope of the present invention, as long as it is an inert material in relation to the content of the gases to be captured. Said gas inlet line (2) may be manufactured from a single material or from a combination of materials without limiting the scope of the present invention. For example, and without limiting the scope of the present invention, said gas inlet line may be manufactured from a material which is selected from the group consisting of steel, stainless steel, copper, bronze, Teflon, glass, ceramics, as well as a combination thereof.

Figures 2, 3, 4, 5:
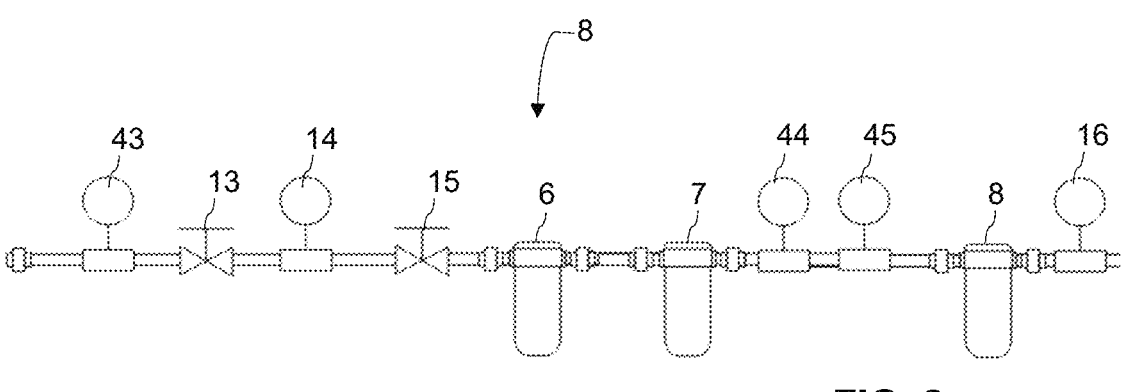
FIG. 2 shows a schematic illustration of a first embodiment of the purification unit which is the subject matter of the present invention.
FIG. 3 shows an illustration of a first embodiment of the coupling means to a fermentation vessel forming part of the gas inlet line in an embodiment of the system which is the subject matter of the present invention.
FIG. 4 shows a front exploded view of a first embodiment of the third filter forming part of the purification unit which is the subject matter of the present invention.
FIG. 5 shows a schematic longitudinal cutaway view of a first embodiment of the third filter forming part of the purification unit which is the subject matter of the present invention.

In a preferred embodiment, without limiting the scope of the present invention, said gas inlet line (2) has coupling means (20) to a fermentation vessel. Said coupling means (20) allow a suitable capture of the gases coming from said fermentation vessel. For example, without limiting the scope of the present invention, FIG. 3 illustrates a preferred embodiment of the inlet line (2) forming part of the present invention wherein coupling means (20) are provided to a fermentation vessel. Said coupling means (20) comprise a cylindrical bellows (21) which expands or contracts depending on the amount of gas that the fermentation process generates. The material from which said cylindrical bellows (21) is manufactured does not limit the scope of the present invention. Additionally, without limiting the scope of the present invention, said coupling means (20) may comprise a conical connector (22) downstream of said cylindrical bellows (21) and a quick release clamp (23) between said conical connector (22) and a duct (24) forming part of said gas inlet line (2).

Additionally, without limiting the scope of the present invention, said gas inlet line (2) may have one or more sensors of one or more parameters of the gas flowing through said gas inlet line (2), operatively connected to said gas inlet line (2). For example, and without limiting the scope of the present invention, said gas inlet line (2) may comprise flow sensors, pressure sensors, gas concentration sensors, temperature sensors, as well as a combination thereof.

The nature of said sensors does not limit the scope of the present invention. For example, when said sensor is a flow sensor, said flow sensor may be chosen from the group consisting of anemometers, mass flow sensors, electromagnetic sensors, among others. On the other hand, when said sensor is a pressure sensor, said sensor may be a membrane sensor, differential sensor, piezoelectric sensor, among others. When said sensor is a gas concentration sensor, said sensor may be an electrochemical sensor, a mass spectrometer, among others. Finally, when said sensor is a temperature sensor, said sensor may be a thermocouple, a platinum resistance thermometer, a bimetallic sensor, among others.

In a preferred embodiment, without limiting the scope of the present invention, said gas inlet line (2) has a pressure sensor (10) operatively connected thereto.

Moreover, said gas inlet line (2) may comprise one or more flow interruption valves operatively connected thereto. Said valves may be unidirectional or bidirectional without limiting the scope of the present invention. For example, said gas inlet line may comprise a valve which is selected from the group consisting of elliptical valves, needle valves, electro-pneumatic valves, butterfly valves, as well as combinations thereof. In a preferred embodiment, said gas inlet line (2) comprises a valve (11) operatively connected thereto.

In those preferred embodiments in which said gas inlet line (2) has a pressure sensor (10) and a valve (11), the relative position between said pressure sensor (10) and said valve (11) does not limit the scope of the present invention. In a preferred embodiment, said valve (11) is positioned downstream of said pressure sensor (10). Said preferred embodiment allows, for example and without limiting the scope of the present invention, keeping said gas inlet line (2) isolated from the accumulation unit (3) by closing said valve (11) until the pressure measured by said pressure sensor (10) exceeds a certain threshold value.

In those preferred embodiments in which the system (1) has a plurality of gas inlet lines (2a, 2b, 2c), the system (1) may, additionally and without limiting the scope of the present invention, comprise a plurality of unidirectional valves (11a, 11b, 11c), each of said unidirectional valves (11a, 11b, 11c) operatively connected to a corresponding gas inlet line (2a, 2b, 2c) of said plurality of gas inlet lines (2a, 2b, 2c).

In other preferred embodiments, without limiting the scope of the present invention, the system (1) may comprise a volumetric flow sensor connected between said gas inlet line (2) and the accumulation unit (3). This configuration is advantageous in that it allows measuring the amount of gas obtained from the $CO_2$ source and that enters said accumulation unit (3). In those preferred embodiments in which the system (1) comprises a plurality of gas inlet lines (2a, 2b, 2c), the system (1) may comprise a single common volumetric flow sensor for said plurality of gas inlet lines (2a, 2b, 2c) or a volumetric flow sensor for each of the gas inlet lines (2a, 2b, 2c) forming said plurality without limiting the scope of the present invention.

As previously mentioned, said gas inlet line (2) is connected to the inlet (31) of the accumulation unit (3) forming part of the system (1) which is the subject matter of the present invention. The manner in which said connection is provided does not limit the scope of the present invention. For example, and without limiting the scope of the present invention, said inlet (31) of said accumulation unit (3) and said gas inlet line (2) may be connected by means of a quick release clamp.

Said accumulation unit (3) has an inlet (31), an outlet (32), and comprises an accumulation tank (33). Said accumulation unit (3), additionally and without limiting the scope of the present invention, may comprise a compressor (34) between said inlet (31) and said accumulation tank (33), which allows increasing the gas pressure inside said accumulation tank (33).

However, in those preferred embodiments in which the system (1) comprises a plurality of gas inlet lines (2a, 2b, 2c) and a coupling connected between said gas inlet lines (2a, 2b, 2c) and said inlet (31) of said accumulation unit (3), said compressor (34) may be positioned, without limiting the scope of the present invention, between the outlet of said coupling and said inlet (31) of said accumulation unit (3).

The shape, dimensions, and materials from which said accumulation unit (3) is manufactured does not limit the scope of the present invention. For example, and without limiting the scope of the present invention, said inlet (31) and said outlet (32) may comprise one or more ducts connected to each other for gas circulation. Said ducts may be rigid or flexible, as well as a combination thereof, without limiting the scope of the present invention. Said accumulation unit (3) may be manufactured from a single material or from a combination of materials without limiting the scope of the present invention. For example, and without limiting the scope of the present invention, said accumulation unit (3) may be manufactured from a material which is selected from the group consisting of steel, stainless steel, copper, bronze, Teflon, glass, ceramics, as well as a combination thereof.

Additionally, without limiting the scope of the present invention, said accumulation unit (3) may have one or more sensors of one or more parameters of the gas accumulating in said accumulation unit (3), operatively connected to said accumulation unit (3). For example, and without limiting the scope of the present invention, said accumulation unit (3) may comprise flow sensors, pressure sensors, gas concentration sensors, temperature sensors, as well as a combination thereof.

The nature of said sensors does not limit the scope of the present invention. For example, when said sensor is a flow sensor, said flow sensor may be chosen from the group consisting of anemometers, mass flow sensors, electromagnetic sensors, among others. On the other hand, when said sensor is a pressure sensor, said sensor may be a membrane sensor, differential sensor, piezoelectric sensor, among others. When said sensor is a gas concentration sensor, said sensor may be an electrochemical sensor, a mass spectrometer, among others. Finally, when said sensor is a temperature sensor, said sensor may be a thermocouple, a platinum resistance thermometer, a bimetallic sensor, among others.

In a preferred embodiment, without limiting the scope of the present invention, said accumulation unit (3) has a second pressure sensor (12) operatively connected thereto. The position within said accumulation unit (3) to which said second pressure sensor (12) is connected does not limit the scope of the present invention and can be positioned either on the inlet (31), on the outlet (32), or on the accumulation tank (33) of said accumulation unit (3).

Moreover, said accumulation unit (3) may comprise one or more flow interruption valves, vent valves or overpressure valves operatively connected thereto. Said valves may be unidirectional or bidirectional without limiting the scope of the present invention.

In the context of the present invention, a vent valve will be understood as a valve which connects a unit or portion of the system (1), which is the subject matter of the present invention, with the surrounding environment and which, when opened, allows the bidirectional circulation of gas. On the other hand, in the context of the present invention, an overpressure valve will be understood as a normally closed valve, which connects a unit or portion of the system (1), which is the subject matter of the present invention, with the surrounding environment and which opens when the pressure difference between said unit or portion and the surrounding environment exceeds a certain threshold value.

When said accumulation unit (3) comprises a flow interruption valve or a vent valve, said valve may be selected from the group consisting of elliptical valves, needle valves, electro-pneumatic valves, butterfly valves, as well as combinations thereof. In a preferred embodiment, said accumulation unit (3) comprises a flow interruption valve (13) operatively connected to the outlet (32) of said accumulation unit (3).

In those preferred embodiments in which said accumulation unit (3) has a second pressure sensor (12) and a flow interruption valve (13), the relative position between said second pressure sensor (12) and said flow interruption valve (13) does not limit the scope of the present invention. In a preferred embodiment, said flow interruption valve (13) is positioned downstream of said second pressure sensor (12). Said preferred embodiment allows, for example and without limiting the scope of the present invention, keeping said accumulation unit (3) isolated from the purification unit (4) by closing said flow interruption valve (13) until the pressure measured by said second pressure sensor (12) exceeds a certain threshold value.

The system (1), which is the subject matter of the present invention, further comprises a purification unit (4) downstream of said accumulation unit (3). All options described for the purification unit (4) as part of the system (1) are applicable to the purification unit (4) as an independent subject matter of invention, without limiting the scope of the present invention. Said purification unit (4) comprises an inlet (41) which is connected downstream of the accumulation unit (3) and an outlet (42).

The shape, dimensions, and material of said purification unit (4) as well as of its various components do not limit the scope of the present invention. For example, and without limiting the scope of the present invention, said inlet (41) and said outlet (42) may comprise one or more ducts connected to each other for gas circulation. Said ducts may be rigid or flexible, as well as a combination thereof, without limiting the scope of the present invention. Said purification unit (4) may be manufactured from a single material or from a combination of materials without limiting the scope of the present invention. For example, and without limiting the scope of the present invention, said purification unit (4) may be manufactured from a material which is selected from the group consisting of steel, stainless steel, copper, bronze, Teflon, glass, ceramics, as well as a combination thereof.

Additionally, without limiting the scope of the present invention, said purification unit (4) may have one or more sensors of one or more parameters of the gas being purified in said purification unit (4), operatively connected to said purification unit (4). For example, and without limiting the scope of the present invention, said purification unit (4) may comprise flow sensors, pressure sensors, gas concentration sensors, temperature sensors, as well as a combination thereof.

The nature of said sensors does not limit the scope of the present invention. For example, when said sensor is a flow sensor, said flow sensor may be chosen from the group consisting of anemometers, mass flow sensors, electromagnetic sensors, among others. On the other hand, when said sensor is a pressure sensor, said sensor may be a membrane sensor, differential sensor, piezoelectric sensor, among others. When said sensor is a gas concentration sensor, said sensor may be an electrochemical sensor, a mass spectrometer, among others. Finally, when said sensor is a temperature sensor, said sensor may be a thermocouple, a platinum resistance thermometer, a bimetallic sensor, among others.

In a preferred embodiment, without limiting the scope of the present invention, said purification unit (4) may comprise a first $CO_2$ concentration sensor (14) operatively connected to said inlet (41) of said purification unit (4). In another preferred embodiment, without limiting the scope of the present invention, said purification unit (4) may comprise a second $CO_2$ concentration sensor (16) operatively connected to an outlet of the third filter (8) of said purification unit (4).

On the other hand, said purification unit (4) may comprise one or more flow interruption valves, vent valves, or overpressure valves operatively connected thereto or to any of its components. Said valves may be unidirectional or bidirectional without limiting the scope of the present invention.

When said purification unit (4) comprises a flow interruption valve or a vent valve, said valve may be selected from the group consisting of elliptical valves, needle valves, electro-pneumatic valves, butterfly valves, as well as combinations thereof. In a preferred embodiment, said accumulation unit (4) may comprise a third valve (15) operatively connected to the inlet (41) of said purification unit (4). In another preferred embodiment, without limiting the scope of the present invention, said purification unit (4) may additionally comprise a fourth valve (17) operatively connected to the outlet of the third filter (8).

In those preferred embodiments in which said purification unit (4) has a first $CO_2$ concentration sensor (14) and a third valve (15), the relative position between said first $CO_2$ concentration sensor (14) and said third valve (15) does not limit the scope of the present invention. In a preferred embodiment, said third valve (15) is positioned downstream of said first $CO_2$ concentration sensor (14). Said preferred embodiment allows, for example and without limiting the scope of the present invention, keeping said purification unit (4) isolated from said accumulation unit (3) by closing said third valve (15) until the $CO_2$ concentration measured by said first $CO_2$ concentration sensor (14) exceeds a certain threshold value.

In those preferred embodiments in which said purification unit (4) has a second $CO_2$ concentration sensor (16) and a fourth valve (17), the relative position between said second $CO_2$ concentration sensor (16) and said fourth valve (17) does not limit the scope of the present invention. In a preferred embodiment, said fourth valve (17) is positioned downstream of said second $CO_2$ concentration sensor (16). Said preferred embodiment allows, for example and without limiting the scope of the present invention, keeping said purification unit (4) isolated from the storage unit (5) by closing said fourth valve (17) until the $CO_2$ concentration measured by said second $CO_2$ concentration sensor (16) exceeds a certain threshold value.

In other preferred embodiments, said purification unit (4) may comprise, additionally and without limiting the scope of the present invention, an 02 concentration sensor (25) operatively connected to the outlet of the third filter (8) of said purification unit (4). Said $O_2$ concentration sensor (25) allows, advantageously and without limiting the scope of the present invention, verifying that the $O_2$ content in the gas leaving the purification unit (4) remains below a tolerance value.

In other preferred embodiments, said purification unit (4) may comprise, additionally and without limiting the scope of the present invention, an $N_2$ concentration sensor (26) operatively connected to the outlet of the third filter (8) of said purification unit (4). Said $N_2$ concentration sensor (26) allows, advantageously and without limiting the scope of the present invention, controlling that the $N_2$ content in the gas leaving the purification unit (4) is kept below a tolerance value.

Said purification unit (4) may comprise, additionally and without limiting the scope of the present invention, a vent valve (18) operatively connected to the outlet of said third filter (8). Said vent valve (18) allows, advantageously and without limiting the scope of the present invention, the venting to the environment of the gas leaving the third filter (8) when the $CO_2$ content is below a tolerance value, as will be explained in detail below.

Said purification unit (4) comprises three filters (6, 7, 8). A first filter (6) has a first container and a first filler material, said filler material being silica. Said first filter (6), which will be named indistinctly as silica filter (6) without limiting the scope of the present invention, allows the capture of the water molecules contained in the gas to be captured and purified. In this way, at the outlet of said silica filter (6) a gas depleted in water and, therefore, enriched in $CO_2$ and $N_2$ is obtained.

Said purification unit (4) has, additionally, a second filter (7) downstream of said first filter (6), which has a second container and a second filler material, said filler material being a zeolite. Said second filter (7), which will be named indistinctly as zeolite filter (7) without limiting the scope of the present invention, allows the capture of organic gas molecules and easily oxidizable gases. In this way, at the outlet of said silica filter (6) a gas highly enriched in $CO_2$ and $N_2$ is obtained.

The purification unit (4) also has a third filter (8) downstream of said second filter (7), which has a third container (81) and a third filler material, said third filler material being a metal-organic framework (MOF) modified with activated carbon. Said third filter (8), which will be named indistinctly as MOF filter (8) without limiting the scope of the present invention, allows, advantageously and without limiting the scope of the present invention, the selective adsorption on said third filler material of $CO_2$ in relation to $N_2$. Said selective adsorption allows, advantageously and without limiting the scope of the present invention, the subsequent release of said $CO_2$ for storage. Thus, in a first stage, the gas at the outlet of said MOF filter (8) is depleted in $CO_2$ and enriched in $N_2$.

In those preferred embodiments in which said purification unit (4) comprises a vent valve (18), it is possible, advantageously and without limiting the scope of the present invention, to vent into the environment said gas depleted in $CO_2$ and enriched in $N_2$ by opening said vent valve (18).

However, after a processing time, in which the initial mixture of $CO_2$ and $N_2$ enters the filter, the amount of $CO_2$ adsorbed on said third filler material will reach levels close to its adsorption capacity. At this stage, it is desirable to desorb $CO_2$ from said third filler material. For this, said third filter (8) has, additionally, a heating element (82) thermally coupled to said third filler material.

Figure 6:
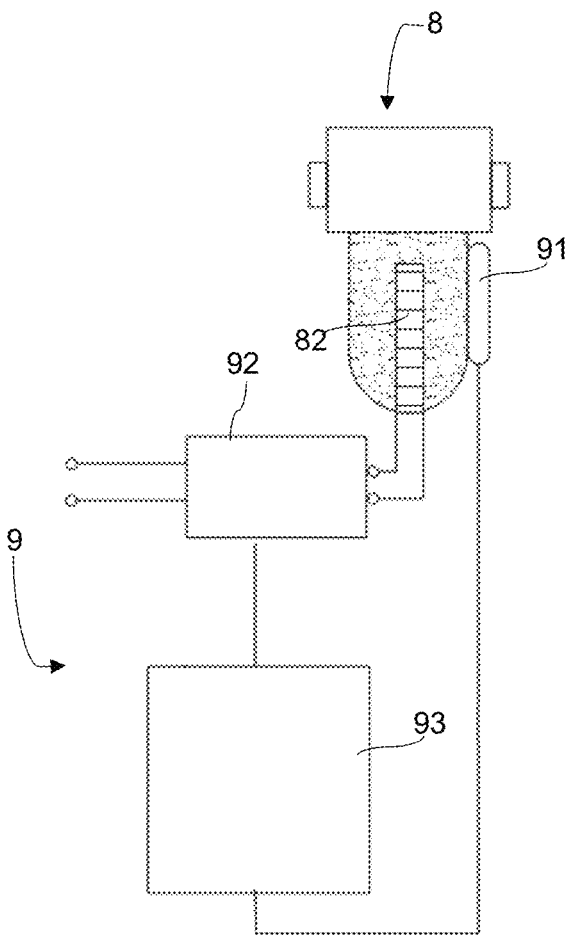
FIG. 6 shows a schematic view of a second embodiment of the third filter forming part of the purification unit, in conjunction with the control means of the heating element forming part of the system which is the subject matter of the present invention.

In the context of the present invention, it will be understood that said heating element (82) is thermally coupled to said third filler material when a temperature increase of said heating element (82) produces the desorption of $CO_2$ from said third filler material. Said heating element (82) may be arranged either on the inside or on the outside of said third container (81), as well as a combination of both arrangements, without limiting the scope of the present invention. For example, and without limiting the scope of the present invention, FIGS. 4 to 6 show a third filter (8) in which said heating element (82) is disposed inside said third container.

FIGS. 4 and 5 illustrate a preferred embodiment of the third filter (8) forming part of the purification unit (4) which is subject matter of the present invention. FIG. 4 illustrates an exploded view of said third filter (8), while FIG. 5 illustrates an assembled view of said third filter (8). In this preferred embodiment, without limiting the scope of the present invention, said third filter (8) has a two-part container (81), a base (811) containing the third filler material, and a lid (812) containing said heating element (82). The base (811), in addition, has a gas inlet (813), while the lid (812) has a gas outlet (814) and a vent valve (18). The coupling between said base (811) and said lid (812) is obtained by means of a male-female threaded connection (815).

Regarding the heating element (82), the nature of said heating element (82) does not limit the scope of the present invention and will depend, among other aspects and without limiting the scope of the present invention, on the shape and dimensions of said third container (81), as well as on whether, by design choice, said heating element (82) is arranged inside or outside said third container (81). For example, and without limiting the scope of the present invention, said heating element (82) may be selected from the group formed by heating tapes, heating plates, incandescent filaments, infrared lamps, electrical resistances, as well as a combination thereof.

Additionally, and in order to control the actuation of said heating element (82), said purification unit (4) additionally comprises control means (9) of said heating element (82). Said control means (9) may be manual or automatic, without limiting the scope of the present invention. Additionally, said control means (9) may comprise one or more elements, without limiting the scope of the present invention.

For example, and without limiting the scope of the present invention, said control means (9) may comprise, on the one hand, temperature sensing elements inside said third filter and, on the other hand, power supply elements of said heating element (82). Said control means (9), for example and without limiting the scope of the present invention, may be selected from the group formed by thermostats, optocouplers, solid state relays, PID temperature controllers, ON-OFF temperature controllers, as well as combinations thereof.

In a preferred embodiment, without limiting the scope of the present invention, said control means (9) comprise a temperature sensor (91), a solid state relay (92) operatively connected to said heating element (82) and a temperature controller (93) connected to said temperature sensor (91) and to said solid state relay (92).

In a preferred embodiment, in addition and without limiting the scope of the present invention, when the system (1) that is the subject matter of the present invention comprises pressure or gas concentration sensors, said control means (9) may, additionally and without limiting the scope of the present invention, be operatively connected to said pressure or gas concentration sensors, in such a way as to obtain a reading of said pressure or gas concentration value from said sensors. Similarly, when the system (1) that is the subject matter of the present invention comprises flow interruption valves or vent valves, without limiting the scope of the present invention, said control means (9) may, additionally and without limiting the scope of the present invention, be operatively connected to said valves, in such a way that said control means (9) may control the opening or closing of said valves. Additionally, in those preferred embodiments in which the system (1) which is the subject matter of the present invention comprises one or more compressors, and without limiting the scope of the present invention, said control means (9) may be operatively connected to said compressors, in such a way that said control means (9) may control the operation of said compressors.

Said preferred embodiments allow, advantageously and without limiting the scope of the present invention, the automation in the operation of the system that is the subject matter of the present invention.

On the other hand, as previously mentioned, the third filler material is a metal-organic framework modified with activated carbon. Any metal-organic framework modified with activated carbon that allows for the selective capture of $CO_2$ versus $N_2$ can be used without limiting the scope of the present invention. For example, and without limiting the scope of the present invention, said metal-organic framework may be selected, without being limited to, from the group consisting of: MOF-5, IRMOF-1, Mg-MOF-74, HKUST-1 and CuBTC, as well as combinations thereof. In a preferred embodiment, said metal-organic framework may have a metal center that is selected from the group consisting of Ni, Cu and Zn, as well as a combination thereof; and an organic ligand that is selected from the group consisting of 1,4-benzenedicarboxylate ($H_2BDC$), tetrabromo-catechol ($H_2TBC$), as well as a combination thereof. In a more preferred embodiment, without limiting the scope of the present invention, said metal-organic framework is Ni-MOF-5, having the formula $Ni_xZn_{4-x}O(BDC)_3$ (0<x<4). In a still more preferred embodiment, said metal-organic framework has the formula $NiZn_3O(BDC)_3$.

The system (1), which is the subject matter of the present invention, further comprises a storage tank (5) for carbon dioxide, having an inlet (51) connected downstream of the purification unit (4).

The shape, dimensions and materials from which said storage tank (5) is manufactured do not limit the scope of the present invention. For example, and without limiting the scope of the present invention, said inlet (51) may comprise one or more ducts connected to each other for gas circulation. Said ducts may be rigid or flexible, as well as a combination thereof, without limiting the scope of the present invention. Said storage tank (5) may be manufactured from a single material or from a combination of materials without limiting the scope of the present invention.

For example, and without limiting the scope of the present invention, said storage tank (5) may be made of a material which is selected from the group consisting of steel, stainless steel, copper, bronze, Teflon, glass, ceramics, as well as a combination thereof.

Additionally, without limiting the scope of the present invention, said storage tank (5) may have one or more sensors of one or more parameters of the gas being stored in said storage tank (5), operatively connected to said storage tank (5). For example, and without limiting the scope of the present invention, said storage tank (5) may comprise flow sensors, pressure sensors, gas concentration sensors, temperature sensors, as well as a combination thereof.

The nature of said sensors does not limit the scope of the present invention. For example, when said sensor is a flow sensor, said flow sensor may be chosen from the group consisting of anemometers, mass flow sensors, electromagnetic sensors, among others. On the other hand, when said sensor is a pressure sensor, said sensor may be a membrane sensor, differential sensor, piezoelectric sensor, among others. When said sensor is a gas concentration sensor, said sensor may be an electrochemical sensor, a mass spectrometer, among others. Finally, when said sensor is a temperature sensor, said sensor may be a thermocouple, a platinum resistance thermometer, a bimetallic sensor, among others.

Moreover, said storage tank (5) may comprise one or more flow interruption valves, vent valves or overpressure valves operatively connected thereto. Said valves may be unidirectional or bidirectional without limiting the scope of the present invention.

When said storage tank (5) comprises a flow interruption valve or a vent valve, said valve may be selected from the group formed by elliptical valves, needle valves, electropneumatic valves, butterfly valves, as well as combinations thereof.

Additionally, in a preferred embodiment and without limiting the scope of the present invention, the system (1), which is the subject matter of the present invention, may comprise a compressor (19) operatively connected between said purification unit (4) and said storage tank (5) which allows increasing the pressure of the gas inside said storage tank (5).

According to the previously detailed description, it is possible to obtain a $CO_2$ capture and purification system (1), as well as a purification unit (4) of said system (1) which allow overcoming the deficiencies of the prior art.

It should be understood that different options described for different technical features can be combined with each other, or with other options foreseen by a person with average knowledge in the technical field, in any manner, without limiting the scope of the present invention.

Hereinafter, examples of embodiments of the present invention will be presented. It should be understood that such examples are included in order to provide a better understanding of the present invention, but do not limit the scope of protection requested. Additionally, technical features described in different examples may be combined with each other, or with other previously described options, in any manner, without limiting the scope of the present invention.

Example 1: Providing a System for the Capture and Purification of Gases from Fermentation Processes A gas capture system was provided as schematically illustrated in FIG. 1. Said system comprises a plurality of gas inlet lines (2a, 2b, 2c), each comprising coupling means (20a, 20b, 20c) to a fermentation vessel. Each of said plurality of gas inlet lines (2a, 2b, 2c) further comprises a pressure sensor (10a, 10b, 10c) and a corresponding unidirectional flow interruption valve (11a, 11b, 11c).

Said plurality of inlet lines (2a, 2b, 2c) are connected, by means of a compressor (34) to an accumulation tank (33) of the accumulation unit (3). Said accumulation unit (3), in addition, has a second pressure sensor (12), a vent valve (35), and an overpressure valve (36) connected to said accumulation tank (33).

Said accumulation unit is then connected to the purification unit (4) which has a first silica filter (6), a second zeolite filter (7), and a third Ni-MOF-5 filter (8) modified with activated carbon. Said third filter (8), in addition, has a heating band thermally coupled to said Ni-MOF-5 filler modified with activated carbon. A vent valve (18) and a flow interruption valve (17) are provided at the outlet of said third filter (8). Downstream of said flow interruption valve (17), three concentration sensors are provided, namely a $CO_2$ concentration sensor (16), an $O_2$ concentration sensor (25), and an $N_2$ concentration sensor (26). Downstream of said sensors, a compressor (19) is provided that connect the outlet of said third filter (8) to the storage tank (5). The storage tank (5) has, additionally, a vent valve (52), an overpressure valve (53), a pressure sensor (54), and a temperature sensor (55).

Example 2: Control of the $CO_2$ Capture and Purification System

In the system described in the above example, control means were provided (not illustrated in FIG. 1), which were operatively connected to all sensors (10a, 10b, 10c, 12, 16, 25, 26, 54, 55), all valves (11a, 11b, 11c, 15, 17, 18, 35, 52, 53), and all compressors (19, 34) of the system described in Example 1. Furthermore, said control means were connected to the heating element (82) of the MOF filter (8) of the purification unit (4).

Furthermore, said control means allow monitoring the control variables during the fermentation process. Additionally, a communication software was provided to allow the visualization of the information.

Example 3: Extraction of Gases from a Plurality of Fermentation Vessels

As previously mentioned, each of the gas inlet lines (2a, 2b, 2c) of the system of Example 1 has corresponding coupling means (20a, 20b, 20c) which are schematically illustrated in FIG. 3. Said coupling means (20) have a rigid ring base (25) which allows adjusting to the different diameters of the vessels by means of an adjustable lock. On said ring base a corrugated fabric (cylindrical bellows 21) is provided, and on said corrugated fabric a conical connector (22) is provided, which allows the connection of said corrugated fabric, by means of a quick release clamp (23), with a gas outlet duct (24), which is part of the gas inlet line (2).

At the moment of maximum fermentation, the pressure inside the fermentation vessel increases, thereby expanding the corrugated fabric. Furthermore, the measurement of the pressure sensors (10a, 10b, 10c) allows the opening of the corresponding valves (11a, 11b, 11c) when the pressure exceeds a threshold value. However, in order to avoid the repetitive opening and closing of the valves (11a, 11b, 11c) when the pressure is around said threshold value, tolerance values were also defined that allow obtaining a hysteresis band in the opening or closing of said valves (11a, 11b, 11c).

Example 4: Gas Filtration-Purification

FIG. 2 shows a schematic illustration of a second embodiment of the purification unit (4) of the system (1). A pressure sensor (43) is observed, followed by a first valve (13). This set of pressure sensor (43) and valve (13) allows obtaining a reference of the pressure in the accumulation unit (3). Next, a $CO_2$ concentration sensor (14) and a second valve (15) are observed. This allows obtaining a gas sample, by opening the valve (13) and measuring the $CO_2$ concentration in the gas coming from the fermentation vessel, before its passage to the filter assembly.

Once a $CO_2$ concentration greater than a reference threshold value has been measured, the second valve (15) is opened and the gas flows through the silica filter (6), where water vapor is trapped, and through the zeolite filter (7), where easily oxidizable gases are captured. At the outlet of the zeolite filter (7), a temperature sensor (44) and a volumetric flow sensor (45) are placed, which allow characterizing the gas before it enters the MOF filter (8). Subsequently, the gas flows through the MOF filter (8), where $CO_2$ is captured in the third filler material, Ni-MOF-5 modified with activated carbon. At the outlet of the MOF filter (8) ¡ a $CO_2$ concentration sensor (16) is placed, which allows monitoring the gas purification process.

Example 5: Desorption of $CO_2$ by Thermal Means

While $CO_2$ is being captured by the third filler material, Ni-MOF-5 modified with activated carbon, the gas stream at the outlet of the MOF filter (8) contains mainly air ($N_2$ and $O_2$) and $CO_2$ in a much lower concentration than the gas entering the purification unit (4). Said gas stream, containing mainly air, is released to the environment by opening the vent valve (18) and closing the flow shut-off valve (17).

Once all the air has passed through, the $CO_2$ adsorbed on the MOF filter (8) is then released. For this, the vent valve (18) is closed, the temperature of the MOF filter (8) is increased, which causes the desorption of $CO_2$ from the third filler material, and the flow interruption valve (17) is opened.

FIG. 6 shows a schematic illustration of the assembly of the third filter (8), the heating element (82), and the control means (9). The heating element (82) is a heating band arranged inside the third filter (8), while the control means (9) comprise a temperature sensor (91) coupled to the outside of the third filter (8), a solid state relay (92) operatively connected to said heating element (82) and to an electrical power source; and a temperature controller (93) connected to said temperature sensor (91) and to said solid state relay (92).

Said temperature controller (93) allows defining a temperature value to be reached by said third filter (8), as well as a temperature increase ramp. In this example of embodiment, said temperature controller (93) executes a PID (Proportional-Integral-Derivative) type control algorithm.

Example 6: Obtaining the Ni-MOF-5 Filler Material Modified with Activated Carbon To obtain the third filler material, Ni-MOF-5 modified with activated carbon, at laboratory scale, 2 g of granular activated carbon; 0.057 g of $Ni(NO_3)_2 \times 6(H_2O)$; 1.614 g of $Zn(NO_3)_2 \times 6(H_2O)$; and 0.3 g of 1,4-benzenedicarboxylic acid ($H_2BCD$) were mixed.

The previously listed precursors were dissolved in 50 ml of N, N-dimethylformamide (DMF) and were subsequently placed in a solvothermal autoclave reactor at a temperature of 140° C. in an oven with air convection for 10 hours.

The synthesized polymer was cooled to room temperature and washed with 50 ml of N, N-dimethylformamide. After washing, the product was activated by solvent exchange, dried at 60° C., and stored in a vacuum desiccator.

Additionally, a second product was obtained by a similar process, but in which the synthesis was carried out by refluxing using microwave radiation in a microwave oven for 60 min.

As a result, Ni-MOF-5 crystals grew directly on the surface of the activated carbon producing a composite between Ni-MOF-5 and activated carbon.

Additionally, oven syntheses were tested at temperatures between 100° C. and 140° C. and residence times between 12 and 24 hours, obtaining crystals within the entire range tested.

Example 7: Characterization of the Ni-MOF-5 Filler Material Modified with Activated Carbon Both materials, obtained by oven synthesis (synthesis temperature of 140° C., residence time of 10 hours) and by microwave synthesis, were characterized using scanning electron microscopy (SEM), X-ray diffraction (XRD), thermogravimetric analysis (TGA), and BET specific surface area determination.

In both cases, a crystalline material was obtained. In the case of oven synthesis, a crystal size between 50 μm and 100 μm was obtained, while in the case of microwave synthesis, a crystal size between 5 μm and 20 μm was obtained.

Both products show high thermal stability. In the case of the oven-synthesized product, the maximum mass loss temperature was 457.9° C., with a mass loss of 8.79%/min. In the case of the microwave-synthesized product, the maximum mass loss temperature was 459.4° C., with a mass loss of 4.72%/min.

In addition, both products have a BET specific surface area of 1985 $m^2/g$.

Example 8: Storage of $CO_2$

The storage of $CO_2$ was performed in a storage tank by gas compression. For this purpose, an intermediate storage tank and a 1.724 MPa (250 psi) output compressor were provided downstream of the storage tank. In addition, an on-off type control system was incorporated that activates the compressor when the pressure on the low pressure side (the accumulation tank) reaches a predetermined value (e.g., 100 or 200 kPa (1-2 Bar)). Tests were performed with storage tanks ranging from 2 to 10 liters, obtaining filling times from 2.5 minutes to 1 hour. The volume of the storage tank was calculated using the ideal gas law, considering a pressure of 1 MPa (10 bar).

The invention claimed is:
1. A system (1) for capture and purification of $CO_2$, said system comprising:
   a gas inlet line (2);
   an accumulation unit (3), having an inlet (31) connected to said gas inlet line (2) and an outlet (32);

a purification unit (4), having an inlet (41) connected downstream of said accumulation unit (3) and an outlet (42); and a storage tank (5), having an inlet (51) connected downstream of said purification unit (4), characterized in that said gas inlet line (2) further comprises a coupling means (20) coupled to a fermentation vessel, said coupling means comprising a cylindrical bellows (21), and said purification unit (4) comprises:

a first filter (6) having a first container and a first filler material;

a second filter (7) having a second container and a second filler material, downstream of said first filter (6);

a third filter (8) having a third container (81) and a third filler material, downstream of said second filter (7), said third filter (8) having, additionally, a heating element (82) thermally coupled to said third filler material; and control means (9) of said heating element (82), wherein said first filler material is silica, wherein said second filler material is zeolite, and wherein said third filler material is a metal-organic framework modified with activated carbon.

2. The system (1) of claim 1, characterized in that it comprises a plurality of gas inlet lines (2a, 2b, 2c) arranged in a parallel manner, and in that said accumulation unit (3) is connected to each of said gas inlet lines (2a, 2b, 2b) of said plurality.

3. The system (1) of claim 2, characterized in that it further comprises a coupling having a plurality of inlets and an outlet; wherein each said inlet of said coupling is connected to a corresponding gas inlet line (2a, 2b, 2c), and in that said outlet of said coupling is connected to said inlet (31) of said 30 accumulation unit (3).

4. The system (1) of claim 3, characterized in that it further comprises a compressor (34) operatively connected between said outlet of said coupling and said inlet (31) of said accumulation unit (3).

5. The system (1) of claim 2, characterized in that it further comprises a plurality of unidirectional valves (11a, 11b, 11c), each of said unidirectional valves (11a, 11b, 11c) operatively connected to a corresponding gas inlet line (2a, 2b, 2c) of said plurality of gas inlet lines (2a, 2b, 2c).

6. The system (1) of claim 1, characterized in that said metal-organic framework has a metal center which is selected from the group consisting of Ni, Cu and Zn, as well as a combination thereof; and an organic ligand which is selected from the group consisting of 1,4-benzenedicarboxylate ($H_2BDC$), tetrabromo-catechol ($H_2TBC$), as well as a combination thereof.

7. The system (1) of claim 6, characterized in that said metal-organic framework is Ni-MOF-5.

8. The system (1) of claim 1, characterized in that said heating element (82) is selected from the group consisting of heating tapes, heating plates, incandescent filaments, infrared lamps, electrical resistors, as well as a combination thereof.

9. The system (1) of claim 1, characterized in that said control means (9) is selected from the group consisting of thermostats, optocouplers, PID temperature controllers, ON-OFF temperature controllers, as well as combinations thereof.

10. The system (1) of claim 1, characterized in that it further comprises:

a first pressure sensor (10) operatively connected to said gas inlet line (2), and a first valve (11) operatively connected to said gas inlet line (2) downstream of said first pressure sensor (10);

a second pressure sensor (12) operatively connected to said accumulation unit (3), and a second valve (13) operatively connected to said outlet (32) of said accumulation unit (3);

a first $CO_2$ concentration sensor (14) operatively connected to said inlet (41) of said purification unit (4), and a third valve (15) operatively connected to said inlet (41) of said purification unit (4) downstream of said first $CO_2$ concentration sensor (14); and a second $CO_2$ concentration sensor (16) operatively connected to an outlet of said third filter (8), and a fourth valve (17) operatively connected to said outlet of said third filter (8).

11. The system (1) of claim 1, characterized in that it further comprises a vent valve (18) operatively connected to an outlet of said third filter (8).

12. The system (1) of claim 1, characterized in that it comprises a compressor (19) operatively connected between said purification unit (4) and said storage tank (5).

* * * * *